(12) United States Patent
Perry

(10) Patent No.: US 8,574,638 B1
(45) Date of Patent: Nov. 5, 2013

(54) RODENTICIDE

(76) Inventor: Stephen C. Perry, Norwood, MA (US)

( * ) Notice: Subject to any disclaimer, the term of this patent is extended or adjusted under 35 U.S.C. 154(b) by 0 days.

(21) Appl. No.: 13/441,652

(22) Filed: Apr. 6, 2012

(51) Int. Cl.
*A01N 65/00* (2009.01)

(52) U.S. Cl.
USPC .......................................... 424/725

(58) Field of Classification Search
None
See application file for complete search history.

(56) References Cited

FOREIGN PATENT DOCUMENTS

KR 2001083629 A * 9/2001

* cited by examiner

*Primary Examiner* — Michael Meller
(74) *Attorney, Agent, or Firm* — Johnson & Martin, P.A.; James David Johnson

(57) ABSTRACT

A rodenticide composition and method for using the same to exterminate rodents. The composition features a mixture of a natural dehydrant capable of dehydrating a rodent that consumes it, a natural carrier matrix, and an optional flavoring. The natural carrier matrix can include a plant-derived grain-based, nut-based, legume-based, or starchy tuber-based composition or combinations or derivatives of the foregoing. The natural dehydrant can be corn gluten meal, soy hydrolysate, soybean oil, castor oil, linseed oil, sodium chloride, cottonseed oil, any other suitable natural dehydrant, combinations thereof, or any other suitable material derived from any of the foregoing. Once the rodenticide composition is prepared, it may be placed in areas frequented by or infested with rodents so as to kill the rodents once they consume the composition.

4 Claims, No Drawings

RODENTICIDE

FIELD OF THE INVENTION

The invention relates to a pesticide. More particularly, the invention relates to a rodenticide useful for exterminating rodents but that is non-toxic to humans and other animals.

BACKGROUND

Pesticides, and particularly rodenticides, can be harmful to humans and other animals that unknowingly consume them or otherwise come into contact with them. In the past, rodenticides ingested intentionally and unintentionally by humans resulted in illness and death. Presently, conventional rodenticides ingested by animals other than the pests (namely, mice and rats) for which they are intended also result in the unintentional killing of those animals. Pet animals and wildlife are both harmed or killed by conventional rodenticide usage.

Vomiting (also called emesis) is a reflexive act caused by coordinated contractions of various muscles that eject stomach contents forcefully through an animal's mouth. Humans and many other animals are capable of vomiting as a natural reaction to purge toxic substances from the body. During vomiting, the muscles of the abdomen and chest contract and the diaphragm spasms downward and inward exerting pressure on the stomach. Next, and nearly simultaneously, the cardiac sphincter, which is a part of the diaphragm surrounding the esophagus, relaxes to assist in opening the esophagus. The longitudinal muscle of the esophagus contracts, which further opens the cardiac sphincter, and the resulting pressure forces contents of the stomach up into the esophagus and out of the animal's mouth.

Rats and many other rodents are unable to vomit, i.e., cannot produce an emetic reflex. Physiologically, rats have a powerful barrier between the stomach and the esophagus but lack sufficient esophageal muscle strength to overcome and open this barrier by force, which is necessary for vomiting. In humans and other animals, the emetic reflex requires that two muscles of the diaphragm contract independently, however, rats are unable to dissociate the activity of these two muscles so that they may produce the independent contractions necessary for vomiting. In addition, rats lack complex neural connections that are present within the brain stem and between brain stem and viscera of humans and other animals that coordinate the numerous muscles that produce the emetic reflex.

While rats are unable to vomit, they do exhibit other behavior-based techniques to avoid consumption of and poisoning by toxic substances. For example, rats learn to avoid certain foods that make them sick. When a rat discovers a new food, the rat consumes a small amount of the food, and if the rat becomes ill after ingesting the food, the rat learns to scrupulously avoid that food in the future. Rats learn to identify the food that is to be avoided by its taste and smell. Rats experiencing nausea also display pica, which is the consumption of clay or other non-food materials. By ingesting clay, some toxins are bound in the rat's stomach, which assists in reducing the effects of the toxin as experienced by the rat.

While rats are unable to vomit, they can regurgitate. Regurgitation is not the same as emesis and does not produce the forceful expulsion of the stomach contents through the esophagus and out of the mouth. In studies, when a rat is fed a diet of bulky food items, when the rat regurgitates stomach contents, the regurgitant is pasty and thick in composition and, as a result of the rat's tongue action, becomes packed as a plug within the rat's pharynx, larynx and esophagus. Because the regurgitant forms a plug, the rat chokes and often dies.

The rat's esophagus includes inner circular and outer longitudinal layers of striated muscle. These two layers of striated muscle become smooth muscle near the esophagus's point of attachment with the rat's stomach. An gastroesophageal barrier separates and closes off the rat's esophagus from its stomach. The gastroesophageal barrier is formed by a crural sling, a lower esophageal sphincter, and intraabdominal esophagus that lie between the crural sling and lower esophageal sphincter. The crural sling is part of the rat's diaphragm and is composed of a U-shaped bundle of fibers that wraps around the esophagus and attaches to the rat's vertebrae so that when the crural sling contracts, the rat's esophagus is pinched closed. The rat's diaphragm is formed by two muscles: the crural sling and the costal muscle, which is attached to the rat's rib cage. The lower esophageal sphincter is a circular muscle that surrounds the base of the esophagus and, at its lower edge, includes muscle fibers that insert into the limiting ridge, as described below.

The stomach of a rat includes two parts, i.e., a forestomach and a corpus. The forestomach is a non-glandular, thin-walled portion that receives the esophagus and serves as an initial holding chamber for food that is consumed. In rats, the forestomach's walls are similar to walls of the rat's esophagus. Unlike the forestomach, the corpus is a glandular, thick-walled section having walls that include secretory glands, which produce mucus and digestive enzymes. In rats, digestion begins in the stomach's corpus. A pyloric sphincter controls movement of stomach contents from the corpus into the intestines. The forestomach and corpus are separated by a limiting ridge (also called the margo plicatus), a low fold of tissue that extends circumferentially from the large curvature of the stomach to the small curvature of the stomach just below the esophagus. At the esophagus, the limiting ridge forms a U-shape that nearly surrounds the esophageal opening into the forestomach and the muscle fibers of the lower esophageal sphincter are inserted into the limiting ridge. Due to this anatomical structure, when a rat's lower esophageal sphincter contracts, both the walls of the rat's esophagus and the sides of the limiting ridge's U-shaped portion are pulled together, which tightly closes the esophageal opening in the rat's stomach thereby preventing stomach contents from being expelled by vomiting.

Pressure at the two ends of a rat's gastroesophageal barrier is much higher than the pressure found in the rat's thorax or abdomen during any phase of the breathing cycle. The strength and pressure of this barrier make reflux in rats nearly impossible although rats may engage in regurgitation. Rats are not capable of vomiting because, for several reasons explained below, they cannot produce the necessary coordinated muscular contractions to overcome this powerful barrier.

Rats are incapable of relaxing the crural sling while simultaneously contracting the remainder of the diaphragm. The rat's esophagus passes through the crural sling, and as explained above, when the crural sling of the diaphragm contracts, the rat's esophagus is pinched tightly closed. Rats are physiologically incapable of dissociating the activity of the crural sling and costal muscle of the their diaphragm, and as a result, a rat cannot relax the crural sling while simultaneously contracting the costal muscle. Instead, in rats as opposed to in humans, both diaphragm muscles always contract or relax together. Rats' inability to separately and selectively control its two diaphragmatic muscles render their bodies incapable of producing the pressure on the stomach necessary to open the crural sling so as to allow their stomach contents to be expelled.

Rats are also unable to open their esophageal sphincter to permit the forceful expulsion of stomach contents during vomiting. In rats, the esophagus consists of a thin, weak unstriated, longitudinal muscle at its point of connection with the stomach, which is not sufficiently strong to open the rat's lower esophageal sphincter so as to allow expulsion of the rat's stomach contents.

Unlike emetic animals (including humans), rats and other nonemetics lack neural connections within the brain and between brainstem and viscera that are necessary to coordinate the numerous muscles that produce the emetic reflex. While the brainstem nuclei and the muscle systems used in vomiting are present in rats and other nonemetics, the complex neural connections between the nuclei or between the brainstem and viscera, which are necessary to produce coordinated muscular contractions required for vomiting, are absent.

A need exists for a rodenticide that is safe and non-toxic if consumed by humans or non-rodent pets and wildlife.

SUMMARY

The invention relates to a rodenticide composition and method for using the same to exterminate rodents. The composition features a mixture of a natural dehydrant capable of dehydrating a rodent that consumes it, a natural carrier matrix, and an optional flavoring. The natural carrier matrix can include a plant-derived grain-based, nut-based, legume-based, or starchy tuber-based composition or combinations or derivatives of the foregoing. The natural dehydrant can be corn gluten meal, soy hydrolysate, soybean oil, castor oil, linseed oil, sodium chloride, cottonseed oil, any other suitable natural dehydrant, combinations thereof, or any other suitable material derived from any of the foregoing. Once the rodenticide composition is prepared, it may be placed in areas frequented by or infested with rodents so as to kill the rodents once they consume the composition.

Because rats do have an emetic reflex as do humans and some other animals, rats cannot experience (i.e., vomiting) to expel the contents of the stomach through the mouth. This physiological feature of rats and some other rodents provides a means for creating non-toxic rodenticides that are safe if consumed by humans, pets, or other non-rodent wildlife while being lethal to rats. The rodenticide composition can be consumed as a food source by rats. After ingestion of the rodenticide composition, dehydration of the rat commences, which causes the rat's blood to thicken as well as circulatory collapse. A rat that has consumed the rodenticide composition will become lethargic and retreat to its burrow where it lapses into a coma and dies. Rodent activity declines as death occurs within 4 to 7 days after regular ingestion of the rodenticide composition.

The rodenticide composition provides an advantage in that it is non-toxic to humans and other animals. The rodenticide composition is also advantageous because it can be prepared efficiently and inexpensively from readily available, plentiful, inexpensive ingredients.

Accordingly, the invention features a rodenticide that includes a mixture of a natural dehydrant and a natural carrier matrix featuring a cellulosic grain-based composition.

In another aspect, the invention can feature the cellulosic grain-based composition including corn cobs, corn starch, corn meal, corn flour, rice, rice flour, wheat flour, any other suitable grain-based material, combinations thereof, or any other suitable material derived from any of the foregoing.

In another aspect, the invention can feature the natural dehydrant including corn gluten meal, soy hydrolysate, soybean oil, castor oil, linseed oil, sodium chloride, cottonseed oil, any other suitable natural dehydrant, combinations thereof, or any other suitable material derived from any of the foregoing.

In another aspect, the invention can feature the natural carrier matrix including a flour or meal of a carbohydrate, lipid, or protein.

In another aspect, the invention can feature at least one of the following optional ingredients: a flavoring, *Medicago sativa sativa* (alfalfa), portabella mushrooms, shitake mushrooms, and poultry egg powder.

The invention also features a rodenticide that includes a mixture of a natural dehydrant and a natural carrier matrix that includes a cellulosic nut-based composition.

In another aspect, the invention can feature the cellulosic nut-based composition including nut meal, any other suitable nut-based material, combinations thereof, or any other suitable material derived from any of the foregoing.

In another aspect, the invention can feature the natural dehydrant including corn gluten meal, soy hydrolysate, soybean oil, castor oil, linseed oil, sodium chloride, cottonseed oil, any other suitable natural dehydrant, combinations thereof, or any other suitable material derived from any of the foregoing.

In another aspect, the invention can feature the natural carrier matrix including a flour or meal of a carbohydrate, lipid, or protein.

In another aspect, the invention can feature at least one of the following optional ingredients: a flavoring, *Medicago sativa sativa* (alfalfa), portabella mushrooms, shitake mushrooms, and poultry egg powder.

The invention also features a rodenticide that includes a mixture of a natural dehydrant and a natural carrier matrix that includes a cellulosic legume-based composition.

In another aspect, the invention can feature the cellulosic legume-based composition including soybean meal, soybean flour, soybean hulls, peanut fiber, peanut powder, peanut oil, peanut flour, peanut shell fibers, *Medicago sativa sativa* (alfalfa), any other suitable legume-based material, combinations thereof, or any other suitable material derived from any of the foregoing.

In another aspect, the invention can feature the natural dehydrant including corn gluten meal, soy hydrolysate, soybean oil, castor oil, linseed oil, sodium chloride, cottonseed oil, any other suitable natural dehydrant, combinations thereof, or any other suitable material derived from any of the foregoing.

In another aspect, the invention can feature the natural carrier matrix including a flour or meal of a carbohydrate, lipid, or protein.

In another aspect, the invention can feature at least one of the following optional ingredients: a flavoring, *Medicago sativa sativa* (alfalfa), portabella mushrooms, shitake mushrooms, and poultry egg powder.

The invention also features a rodenticide that includes a mixture of a natural dehydrant and a natural carrier matrix that includes a cellulosic starchy tuber-based composition.

In another aspect, the invention can feature the cellulosic starchy tuber-based composition including potato starch, potato meal, potato flour, any other suitable starchy tuber-based material, combinations thereof, or any other suitable material derived from any of the foregoing.

In another aspect, the invention can feature the natural dehydrant including corn gluten meal, soy hydrolysate, soybean oil, castor oil, linseed oil, sodium chloride, cottonseed oil, any other suitable natural dehydrant, combinations thereof, or any other suitable material derived from any of the foregoing.

In another aspect, the invention can feature the natural carrier matrix including a flour or meal of a carbohydrate, lipid, or protein.

In another aspect, the invention can feature at least one of the following optional ingredients: a flavoring, *Medicago sativa sativa* (alfalfa), portabella mushrooms, shitake mushrooms, and poultry egg powder.

The invention also features a rodenticide composition including a mixture of a natural dehydrant and a natural carrier matrix. The natural dehydrant features a composition that is toxic to rodents and other non-emetic animals but non-toxic to emetics. The natural carrier matrix features a cellulosic composition made from a grain, a legume, a nut, or a starchy tuber.

A method of the invention can be used to exterminate rodents, and the method can include the steps of: (a) preparing a rodenticide composition that includes a mixture of a natural dehydrant and a natural carrier matrix, wherein the natural carrier matrix features a cellulosic composition that is grain-based, nut-based, legume-based, or starchy tuber-based; and (b) placing an amount of the rodenticide composition sufficient to kill a rodent in an area in which the extermination of rodents is desired, wherein the rodent is killed after consuming the rodenticide composition.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control.

DETAILED DESCRIPTION

The present invention is best understood by reference to the description set forth herein. Those skilled in the art will readily appreciate that the detailed description given herein is for explanatory purposes as the invention extends beyond these limited embodiments. For example, in light of the teachings of the present invention, those skilled in the art will recognize a multiplicity of alternate and suitable approaches, depending upon the needs of the particular application, to implement the functionality of any given detail described herein beyond the particular implementation choices in the following embodiments described and shown. That is, numerous modifications and variations of the invention exist that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The present invention is not limited to the particular methodology, compounds, materials, manufacturing techniques, uses, and applications, described herein, as these may vary. The terminology used herein is used for the purpose of describing particular embodiments only, and is not intended to limit the scope of the present invention. As used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means.

All conjunctions used herein are to be understood in the most inclusive sense possible. Thus, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise. Structures described herein are to be understood also to refer to functional equivalents of such structures. Language that may be construed to express approximation should be so understood unless the context clearly dictates otherwise.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "having" should be interpreted as "having at least"; the term "includes" should be interpreted as "includes but is not limited to"; the term "example" is used to provide exemplary instances of the item in discussion, not an exhaustive or limiting list thereof; and use of terms like "preferably," "preferred," "desired," "desirable," or "exemplary" and words of similar meaning should not be understood as implying that certain features are critical, essential, or even important to the structure or function of the invention, but instead as merely intended to highlight alternative or additional features that may or may not be utilized in a particular embodiment of the invention.

Those skilled in the art will also understand that if a specific number of an introduced claim recitation is intended, such an intent will be explicitly recited in the claim, and in the absence of such recitation no such intent is present. For example, as an aid to understanding, the appended claims may contain usage of the introductory phrases "at least one" and "one or more" to introduce claim recitations; however, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C" is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C" is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

All numbers expressing dimensions, quantities of ingredients, reaction conditions, and so forth used in the specification are to be understood as being modified in all instances by the term "about" unless expressly stated otherwise. Accordingly, unless indicated to the contrary, the numerical parameters set forth herein are approximations that may vary depending upon the desired properties sought to be obtained.

The invention provides a rodenticide composition and method for using the same to exterminate rodents. The composition features a mixture of a natural dehydrant capable of dehydrating a rodent that consumes it, a natural carrier matrix, and an optional flavoring. The optional flavoring can be one or more natural or artificial flavors or combinations thereof. The optional flavoring, when included in the composition, may be present in a range of from about 0.1% to about 5% by weight. For example, the optional flavoring could be included in the rodenticide composition in about 0.01, 0.05, 0.09, 0.1, 0.2, 0.25, 0.3, 0.4, 0.41, 0.45, 0.49, 0.5, 0.51, 0.55, 0.59, 0.6, 0.7, 0.75, 0.8, 0.9, 0.91, 0.95, 0.99, or 1 percent by weight.

The natural carrier matrix can feature a flour or meal of a carbohydrate, lipid, or protein. More particularly, the natural carrier matrix can include a plant-derived grain-based composition, a nut-based composition, a legume-based composition, a starchy tuber-based composition, or combinations or derivatives of one or more of the foregoing. The natural carrier matrix can be included in the rodenticide composition in a percentage by weight of about 90% to about 99%. For example, the natural carrier matrix may be incorporated into the rodenticide composition in about 80, 81, 82, 83, 85, 86, 88, 89, 89.1, 89.25, 89.5, 89.7, 89.9, 90, 90.1, 90.25, 90.5, 90.8, 90.9, 91, 92, 92.1, 92.25, 92.5, 92.75, 92.9, 93, 93.1, 93.25, 93.5, 93.75, 93.9, 94, 94.1, 94.25, 94.5, 94.75, 94.9, 95, 95.1, 95.25, 95.5, 95.75, 95.9, 96, 97, 97.1, 97.25, 97.5, 97.75, 97.9, 98, 98.1, 98.25, 98.5, 98.75, 98.9, 99, 99.1, 99.25, 99.5, 99.7, 99.9, or 99.99 percent by weight. In a preferred range, the rodenticide composition can include the natural carrier matrix in a percentage by weight of about 93% to about 99%. In a most preferred range, the rodenticide composition can include the natural carrier matrix in a percentage by weight of about 95% to about 98%.

The natural dehydrant can be corn gluten meal, soy hydrolysate, soybean oil, castor oil, linseed oil, sodium chloride, cottonseed oil, any other suitable natural dehydrant, combinations thereof, or any other suitable material derived from any of the foregoing. The natural dehydrant may be included in the rodenticide composition in a percentage by weight of about 0.5% to about 10%. For example, the natural dehydrant may be incorporated into the rodenticide composition in about 0.05, 0.1, 0.2, 0.25, 0.3, 0.4, 0.41, 0.45, 0.49, 0.5, 0.51, 0.55, 0.59, 0.6, 0.7, 0.75, 0.8, 0.9, 0.91, 0.95, 0.99, 1, 1.01, 1.1, 1.25, 1.5, 1.75, 1.9, 2, 2.1, 2.25, 2.5, 2.75, 2.9, 3, 4, 4.1, 4.25, 4.5, 4.75, 4.9, 5, 5.1, 5.25, 5.5, 5.75, 5.9, 6, 6.1, 6.25, 6.5, 6.75, 6.9, 7, 7.1, 7.25, 7.5, 7.75, 7.9, 8, 9, 9.1, 9.25, 9.5, 9.75, 9.9, 10, 10.1, 10.25, 10.5, 10.75, 10.9, 11, 12, 15, 16, 17, 18, 19, or 20 percent by weight. In a preferred range, the rodenticide composition can include the natural dehydrant in a percentage by weight of about 1% to about 7%. In a most preferred range, the rodenticide composition can include the natural dehydrant in a percentage by weight of about 2% to about 5%. Once the rodenticide composition is prepared, it may be placed in areas frequented by or infested with rodents so as to kill the rodents once they consume the composition.

In one embodiment, the natural carrier matrix can be a cellulosic grain-based composition. The cellulosic grain-based composition can be prepared from corn cobs, corn starch, corn meal, corn flour, rice, rice flour, wheat flour, any other suitable grain-based material, combinations thereof, or any other suitable material derived from any of the foregoing.

In another embodiment, the natural carrier matrix can be a cellulosic nut-based composition. The cellulosic nut-based composition can be prepared from nut meal, any other suitable nut-based material, combinations thereof, or any other suitable material derived from any of the foregoing.

In another embodiment, the natural carrier matrix can be a cellulosic legume-based composition. The cellulosic legume-based composition can be prepared from soybean meal, soybean flour, soybean hulls, peanut fiber, peanut powder, peanut oil, peanut flour, peanut shell fibers, alfalfa, any other suitable legume-based material, combinations thereof, or any other suitable material derived from any of the foregoing.

In another embodiment, the natural carrier matrix can be a cellulosic starchy tuber-based composition. The cellulosic starchy tuber-based composition can be prepared from potato starch, potato meal, potato flour, any other suitable starchy tuber-based material, combinations thereof, or any other suitable material derived from any of the foregoing.

In one example of an exemplary embodiment of the rodenticide composition, the composition can include, in percentages by weight, about 1% white bean powder, about 1% wheat flour, about 5% sweet molasses, and about 93% corn cob powder. Optionally, natural or artificial flavors may also be included.

In an example of another exemplary embodiment of the rodenticide composition, the composition can include, in percentages by weight, about 5% soybean oil, about 5% soybean meal, about 8% soybean flour, about 5% soy molasses, and about 77% soybean hull powder. Optionally, natural or artificial flavors may also be included.

Example 1

In an example of another exemplary embodiment, the rodenticide composition can include corn meal, wheat germ oil, wheat flour, molasses, and corn cob powder. These ingredients can be present, in percentages by weight, of about 0.5% to about 5% corn meal, about 0.5% to about 5% wheat germ oil, about 0.5% to about 10% wheat flour, about 1% to about 15% molasses, and about 60% to about 99% corn cob powder. In a more preferred embodiment containing this set of ingredients, the ingredients can be present, in percentages by weight, of about 0.75% to about 2% corn meal, about 0.75% to about 3% wheat germ oil, about 0.75% to about 6% wheat flour, about 2% to about 12% molasses, and about 68% to about 95% corn cob powder. In a most preferred embodiment containing this set of ingredients, the ingredients can be present, in percentages by weight, of about 1% to about 2% corn meal, about 1% to about 3% wheat germ oil, about 1% to about 6% wheat flour, about 2% to about 5% molasses, and about 84% to about 95% corn cob powder. Optionally, natural or artificial flavors may also be included in any of the embodiments of the rodenticide composition.

Example 2

In an example of another exemplary embodiment, the rodenticide composition can include, in percentages by weight, about 0.5% to about 5% soy bean oil, about 0.5% to about 5% soy bean meal, about 0.5% to about 10% soy bean flour, about 1% to about 15% soy molasses, and about 60% to about 99% soy bean hulls. In a more preferred embodiment containing this set of ingredients, the ingredients of the rodenticide composition can include, in percentages by weight, about 0.75% to about 2% soy bean oil, about 0.75% to about 3% soy bean meal, about 0.75% to about 6% soy bean flour, about 2% to about 12% soy molasses, and about 80% to about 95% soy bean hulls. In a most preferred embodiment containing this set of ingredients, the ingredients of the rodenticide composition can include, in percentages by weight, about 1% to about 2% soy bean oil, about 1% to about 3% soy bean meal, about 1% to about 6% soy bean flour, about 2% to about 5% soy molasses, and about 84% to about 95% soy bean hulls. Optionally, natural or artificial flavors may also be included in any of the embodiments of the rodenticide composition.

In addition to the main ingredients described herein above, the rodenticide composition can include one or more of the following optional ingredients: *Medicago sativa sativa* (alfalfa), portabella mushrooms, shitake mushrooms, and poultry egg powder. *Medicago sativa sativa* (alfalfa) is a natural carrier matrix. Portabella mushrooms, shitake mushrooms, and poultry egg powder are each natural dehydrants. In exemplary embodiments containing one or more of the optional ingredients, in addition to two or more of the main ingredients described herein above, the rodenticide composition can include one or more of the optional ingredients in the following percentages by weight: about 15% to about 99% by weight alfalfa, about 1% to about 20% portabella mushrooms, about 1% to about 20% shitake mushrooms, and about 1% to about 20% poultry egg powder. In more preferred embodiments containing one or more of the optional ingredients, in addition to two or more of the main ingredients described herein above, the rodenticide composition can include one or more of the optional ingredients in the following percentages by weight: about 30% to about 70% by weight alfalfa, about 3% to about 15% portabella mushrooms, about 3% to about 15% shitake mushrooms, and about 3% to about 15% poultry egg powder. In most preferred embodiments containing one or more of the optional ingredients, in addition to two or more of the main ingredients described herein above, the rodenticide composition can include one or more of the optional ingredients in the following percentages by weight: about 45% to about 65% by weight alfalfa, about 5% to about 12% portabella mushrooms, about 5% to about 12% shitake mushrooms, and about 5% to about 12% poultry egg powder.

Indoor and outdoor test trials were conducted using one or more embodiments of the rodenticide composition as described in Examples 1 and 2 above.

Indoor Trial

Prior to treatment using the rodenticide composition, all likely food sources were removed from the indoor testing site. Samples of the rodenticide composition were placed in locations of the indoor testing site where fresh signs of rodent activity were found, e.g., fresh droppings. Sixty grams of the rodenticide composition of Example 1 was placed into each of several small feed trays spaced approximately 36 inches apart throughout the infested indoor area. Activity and mortality was examined by counting dead or moribund species found within 10 feet of the feed trays over a 10-day period. After five days, no fresh droppings were found and three rodent carcasses had been collected. Two of the carcasses were of the common house mouse (*Mus musculus*) and one carcass was of the common brown rat (*Rattus norvegicus*).

Outdoor Trial

Samples of the rodenticide composition were placed in locations of the outdoor testing site fresh signs of rodent activity were found, e.g., fresh droppings and near burrows, runways, feeding places, and at points of entry around the perimeter of a utilized building. Sixty grams of the rodenticide composition of Example 2 were placed in open shallow feed trays or wrapped in cling film and placed in drainpipes, open-ended boxes, or under sheets of metal/wood secured at an angel against a wall (to keep the product dry) at intervals of approximately two yards (72 inches reducing to approximately 1.5 yards in areas of suspected high infestation). Activity and mortality was examined by counting dead or moribund species found within 20 feet of the feed trays over a 10-day period. After six days a dramatic decrease in fresh droppings was recorded and seven rodent carcasses had been collected. Three of the carcasses were of the common house mouse (*Mus musculus*), three carcasses were of the common brown rat (*Rattus norvegicus*), and one carcass was of the common deer mouse (*Peromyscus maniculatus*).

The invention also features a method that can be used to exterminate rodents. In a first step of the method, a rodenticide composition, as described herein above, that includes a mixture of a natural dehydrant and a natural carrier matrix, wherein the natural carrier matrix features a cellulosic composition that is grain-based, nut-based, legume-based, or starchy tuber-based, is prepared. Once the rodenticide composition has been prepared, in a next step of the method, an amount of the rodenticide composition sufficient to kill a rodent is placed in an area in which the extermination of rodents is desired, wherein the rodent is killed after consuming the rodenticide composition.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition for exterminating rats and mice consisting essentially of rodenticide-effective amounts of corn cobs, castor oil, alfalfa, shitake mushrooms and portabella mushrooms.

2. A composition for exterminating rats and mice consisting essentially of rodenticide-effective amounts of corn cobs, corn starch, corn meal, corn flour, corn gluten meal, soy hydrolysate, soybean oil, castor oil, and a component selected from the group consisting of: alfalfa, shitake mushrooms and portabella mushrooms.

3. A composition for exterminating rats and mice consisting essentially of rodenticide-effective amounts of corn cobs, corn starch, corn meal, corn flour, corn gluten meal, soy hydrolysate, soybean oil, castor oil, shitake mushrooms, portabella mushrooms and a component selected from the group consisting of rice, rice flour, wheat flour, linseed oil, sodium chloride, cottonseed oil, alfalfa and poultry egg powder.

4. A composition for exterminating rats and mice consisting essentially of rodenticide-effective amounts of corn cobs, corn gluten meal, wheat flour, and wheat germ oil.

* * * * *